(12) United States Patent
Delenstarr

(10) Patent No.: US 8,077,951 B2
(45) Date of Patent: *Dec. 13, 2011

(54) METHOD AND SYSTEM FOR DYNAMIC, AUTOMATED DETECTION OF OUTLYING FEATURE AND FEATURE BACKGROUND REGIONS DURING PROCESSING OF DATA SCANNED FROM A CHEMICAL ARRAY

(75) Inventor: Glenda C. Delenstarr, Redwood City, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1462 days.

This patent is subject to a terminal disclaimer.

(21) Appl. No.: 11/580,476

(22) Filed: Oct. 12, 2006

(65) Prior Publication Data

US 2008/0089568 A1    Apr. 17, 2008

(51) Int. Cl.
*G06K 9/00* (2006.01)
(52) U.S. Cl. ....................................... 382/129
(58) Field of Classification Search .......... 382/128–131, 382/133, 209, 218; 435/4, 30, 34, 39, 287.2; 702/27–28, 30, 32
See application file for complete search history.

(56) References Cited

U.S. PATENT DOCUMENTS

| | | | |
|---|---|---|---|
| 5,187,753 A * | 2/1993 | Bloomberg et al. | 382/289 |
| 6,014,470 A * | 1/2000 | Matsuda | 382/275 |
| 6,171,797 B1 | 1/2001 | Perbost | |
| 6,180,351 B1 | 1/2001 | Cattell | |
| 6,221,583 B1 | 4/2001 | Kayyem et al. | |
| 6,222,664 B1 | 4/2001 | Dorsel et al. | |
| 6,232,072 B1 | 5/2001 | Fisher | |
| 6,242,266 B1 | 6/2001 | Schleifer et al. | |
| 6,251,685 B1 | 6/2001 | Dorsel et al. | |
| 6,320,196 B1 | 11/2001 | Dorsel et al. | |
| 6,323,043 B1 | 11/2001 | Caren et al. | |
| 6,355,921 B1 | 3/2002 | Staton et al. | |
| 6,371,370 B2 | 4/2002 | Sadler et al. | |
| 6,406,849 B1 | 6/2002 | Dorsel et al. | |
| 6,410,243 B1 | 6/2002 | Wyrick et al. | |
| 6,486,457 B1 | 11/2002 | Dorsel et al. | |
| 6,512,845 B1 * | 1/2003 | Haikin et al. | 382/165 |
| 6,516,276 B1 * | 2/2003 | Ghandour et al. | 702/27 |
| 6,518,556 B2 | 2/2003 | Staton et al. | |
| 6,763,141 B2 * | 7/2004 | Xu et al. | 382/255 |
| 6,768,820 B1 * | 7/2004 | Yakhini et al. | 382/289 |

(Continued)

FOREIGN PATENT DOCUMENTS

WO    WO 93/18186    9/1993

*Primary Examiner* — Gregory M Desire
*Assistant Examiner* — Andrae S Allison

(57) ABSTRACT

A method and system for employing signal-intensity data contained within areas of a scanned image of a chemical array corresponding to features and feature backgrounds in order to determine whether or not the features or feature backgrounds have non-uniform signal intensities and are thus outlier features and outlier feature backgrounds. A signal intensity variance model is provided to dynamically adjust to the signals read from the scanned image of the array. Calculated variance from measured values of the signal intensities and pixel distributions within a feature or feature background is compared to a maximum allowable variance calculated for the feature or feature background based on the dynamically adjusting signal intensity variance model. When the calculated variance (from the measured values) is less than or equal to the maximum allowable variance, the feature or feature background is considered to have acceptable signal-intensity uniformity. Otherwise, the feature or feature background is flagged as an outlier feature or outlier feature background.

24 Claims, 10 Drawing Sheets

U.S. PATENT DOCUMENTS

| | | |
|---|---|---|
| 6,832,163 B2 | 12/2004 | Delenstarr |
| 6,993,172 B2 * | 1/2006 | Connell et al. .............. 382/129 |
| 7,170,644 B2 * | 1/2007 | Loce et al. .............. 358/3.26 |
| 7,206,438 B2 * | 4/2007 | Corson et al. .............. 382/128 |
| 7,330,606 B2 * | 2/2008 | Yakhini et al. .............. 382/294 |
| 7,492,488 B2 * | 2/2009 | Liu .............. 358/406 |
| 2003/0081819 A1 | 5/2003 | Connell et al. |
| 2004/0218793 A1 * | 11/2004 | Corson et al. .............. 382/128 |

* cited by examiner

METHOD AND SYSTEM FOR DYNAMIC, AUTOMATED DETECTION OF OUTLYING FEATURE AND FEATURE BACKGROUND REGIONS DURING PROCESSING OF DATA SCANNED FROM A CHEMICAL ARRAY

BACKGROUND OF THE INVENTION

Chemical array technologies have gained prominence in biological research and are likely to become important and widely used diagnostic tools in the healthcare industry. Currently, chemical-array techniques are most often used to determine the concentrations of particular nucleic-acid polymers in complex sample solutions. Chemical-array-based analytical techniques are not, however, restricted to analysis of nucleic acid solutions, but may be employed to analyze complex solutions of any type of molecule that can be optically or radiometrically scanned and that can bind with high specificity to complementary molecules synthesized within, or bound to, discrete features on the surface of a chemical array.

Scanning of a feature by an optical scanning device or radiometric scanning device generally produces a scanned image comprising a rectilinear grid of pixels, with each pixel having a corresponding signal intensity. It is desirable for the signal intensities, or counts, of pixels within the area of a pixel-based scanned image corresponding to a feature to be relatively uniform. Similarly, it is also desirable for the signal intensities within background regions surrounding features to be relatively uniform. Non-uniform signal intensity distributions generally indicate the occurrence of one or more error or noise conditions that may prevent meaningful data from being collected from the feature.

One current technique for identifying outlier features, or feature backgrounds, involves manual inspection of scanned images and manual flagging of those features or feature backgrounds that appear to be nonuniform, as visually identified by a user/inspector. Additionally, the manual flags may be noted in feature extraction software that further processes the feature and/or background signals, so that the feature extraction software ignores those features and feature backgrounds that are flagged, and does not process the signals therefrom. This technique is very time consuming, tedious, and prone to subjective error, as standards for flagging may vary from user to user.

Another method of identifying outlier features or outlier feature backgrounds is described in U.S. Pat. No. 6,832,163, which is hereby incorporated herein, in its entirety, by reference thereto. This method automatically flags outlier features and outlier local backgrounds if the pixel variance of that feature or local background is determined to be outside of a calculated limit. A toggle parameter is determined from low signal features on the array and a variance limit is calculated from an equation that estimates a pixel model error. The equation that estimates a pixel model error, and includes two terms: a constant term derived from the low signal probes, and a coefficient of variation term that is tuned. Tuning is a process performed by internal developers using many arrays from different lots and experimenters. The constant term is tuned by examining the pixel standard deviation (SD) of low signal features. The coefficient of variation term is a variable term that is optimized by changing a multiplier of the term and then examining resultant output data iteratively as the multiplier is varied each time. The coefficient of variation term is tuned by observing the pixel CV of features (standard deviation of pixel signals/net signal) at the high signal range.

Another method of identifying outlier features or outlier feature backgrounds is described in U.S. Pat. No. 6,993,172, which is hereby incorporated herein, in its entirety, by reference thereto. In this method, the pixel noise or error model has three terms or coefficients, which provide an additional degree of freedom over that described in U.S. Pat. No. 6,832, 163 and may consequently tend to fit the pixel data better. The pixel noise model includes a constant term (C), a Poissonian term (B) and a coefficient of variation (CV) term (A).

The methods described in U.S. Pat. Nos. 6,832,163 and 6,993,172 can be very time consuming, particularly for internal developers, as each array platform must be tuned individually. Variations that occur in array platforms that require re-tuning of the model terms of these methods include different applications of the array (e.g., gene expression versus CGH analysis or location analysis); differences in upstream wet protocols, such as variations in labeling, hybridization or washing of arrays; different scanner manufacturers or models, variable photomultiplier tube settings for different channels for the same array, variable photomultiplier tube settings for different arrays; and variable photomultiplier tube settings for different channels on different scanners.

Thus, designers, manufacturers, and users of chemical arrays have recognized the need for more automated methods for recognizing outlier features and outlier feature backgrounds in scanned images of chemical arrays, that require less setup and tuning than what is currently available.

SUMMARY OF THE INVENTION

Methods, systems and computer readable media for identifying a non-uniform measured signal distribution in a region of a scanned image of a chemical array, include: providing an automatic, dynamically adjustable variance model for measured signal distributions within regions of the chemical array; determining a variance of measured signals within the region; determining whether or not the region contains a non-uniform measured signal distribution by comparing the determined variance of measured signals within the region to the variance model; and displaying results indicating whether or not the region contains a non-uniform measure signal distribution.

In at least one embodiment, the dynamic automatically adjustable variance model includes coefficients of the variance model that are dependent upon a scanner used to scan the image and coefficients that are dependent upon the characteristics of the chemical array, wherein the coefficients that are dependent upon the characteristics of the chemical array are dynamically determined by the model.

A variance threshold may be determined from the automatic, dynamically adjustable variance model, wherein comparing the determined variance of measured signals within the region to the variance model comprises comparing the determined variance of measured signals within the region to the determined variance threshold.

The scanned image comprises pixels, and each pixel associated with a count represents a signal measured from a corresponding portion of the chemical array.

In at least one embodiment, the variance model is a linear combination of model variance terms. These model variance terms include: a variance term arising from non-uniformities associated with target-molecule labeling, feature synthesis, probe molecule application, and other solution and surface chemistry effects; an automatic, dynamically adjusting variance term arising from non-uniformities associated with scanner counting errors, that automatically and dynamically adjusts to the pixels of the scanned image; and an automatic, dynamically adjusting variance term arising from non-uniformities associated with electronic noise in a scanner, background-level signal noise arising from a chemical array substrate, and other noise, that automatically and dynamically adjusts to the pixels of the scanned image.

In at least one embodiment, the variance term arising from non-uniformities associated with target-molecule labeling, feature synthesis, probe molecule application, and other solution and surface chemistry effects is an automatic, dynamically adjusting variable that adjusts to the pixels of the scanned image.

In at least one embodiment, non-uniformities associated with scanner counting errors are modeled by a Poisson distribution.

In at least one embodiment, the variance model is an expression including a mean pixel count for the region as a variable.

The calculation of the variance threshold from the variance model may include assuming a chi-squared distribution for one less than the number of pixels multiplied by the model variance and divided by the theoretical variance of measured signals within the region, and, based on the chi-squared distribution assumption, selecting a threshold variance value below which the determined variance of measured signals within the region has a high probability of indicating an acceptably uniform distribution of measured signals within the region.

The region may be selected from among a feature and a feature background.

In at least one embodiment, the variance model is provided according to chemical and physical properties of the chemical array, electronic and physical properties of a scanning device, and experimental conditions to which the chemical array is exposed.

A method of dynamically tuning a variance model to an instance of a hybridized chemical array, is provided, including the steps of: inputting signal intensity values produced from scanning a region of the hybridized array; defining a variance model as a sum of factors multiplied by multiplicative coefficients, wherein the multiplicative coefficients for the respective factors are each a composite of a scanner-dependent multiplier and an array-dependent multiplier; dynamically calculating the array-dependent multipliers; determining a variance of measured signals within the region; determining whether or not the region contains a non-uniform measured signal distribution by comparing the determined variance of measured signals within the region to the variance model; and displaying results indicating whether or not the region contains a non-uniform measure signal distribution.

In at least one embodiment, the scanner-dependent multipliers are tuned from empirical analysis of large numbers of arrays having different characteristics, such that the scanner-dependent multipliers stay the same in the variance model as long as the same scanner or model of scanner is being used with various arrays, and wherein the array-dependent multipliers are dynamically calculated for each individual array that the variance model is applied to.

A system for identifying a non-uniform measured signal distribution in a region of a scanned image of a chemical array is provided, including: a digital representation of the measured signals in the region of the scanned image of the chemical array stored within a memory component; an automatic, dynamically adjustable variance model for measured signal distributions within regions of the chemical array stored within a memory component; and a computational processing engine that calculates a variance of measured signals within the region and compares the calculated variance with the variance model to determine whether or not the region contains a non-uniform measured signal distribution by comparing the determined variance of measured signals within the region to the variance model.

In at least one embodiment, the automatic, dynamically adjusting variance model further includes a variance threshold to which the computational processing engine compares the calculated variance.

The digital representation of the measured signals in the region of the scanned image of the chemical array may comprise a number of pixels, each pixel associated with a count representing a signal measured from a corresponding portion of the chemical array.

In at least one embodiment, the automatic, dynamically adjusting variance model is a linear combination of model variance terms. These model variance terms include: a variance term arising from non-uniformities associated with target-molecule labeling, feature synthesis, probe molecule application, and other solution and surface chemistry effects; an automatic, dynamically adjusting variance term arising from non-uniformities associated with scanner counting errors, that automatically and dynamically adjusts to the pixels of the scanned image; and an automatic, dynamically adjusting variance term arising from non-uniformities associated with electronic noise in a scanner, background-level signal noise arising from a chemical array substrate, and other noise, that automatically and dynamically adjusts to the pixels of the scanned image.

In at least one embodiment, the variance term arising from non-uniformities associated with target-molecule labeling, feature synthesis, probe molecule application, and other solution and surface chemistry effects is an automatic, dynamically adjusting variable that adjusts to the pixels of the scanned image.

In at least one embodiment, the non-uniformities associated with scanner counting errors are modeled by a Poisson distribution.

In at least one embodiment, the variance model is an expression including a mean pixel count for the region as a variable.

The variance model may be based on chemical and physical properties of the chemical array, electronic and physical properties of a scanning device, and experimental conditions to which the chemical array is exposed.

These and other features of the invention will become apparent to those persons skilled in the art upon reading the details of the methods, systems and computer readable media as more fully described below.

DETAILED DESCRIPTION OF THE INVENTION

Figure 1:
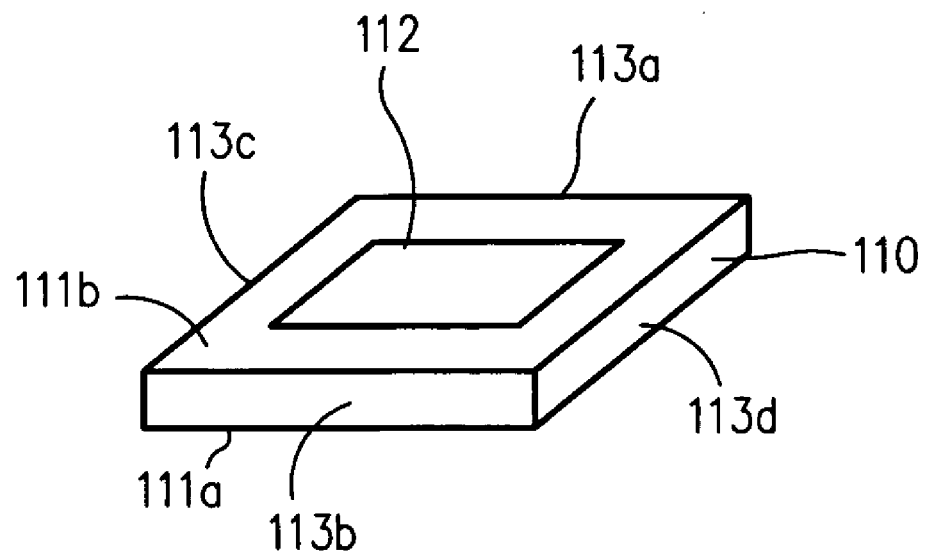
FIG. 1 illustrates an exemplary chemical array.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a feature" includes a plurality of such features and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions and Further Information About Arrays

A chemical "array", unless a contrary intention appears, includes any one, two or three-dimensional arrangement of addressable regions bearing a particular chemical moiety or moieties (for example, biopolymers such as polynucleotide sequences, or other biological targets such as proteins) associated with that region, where the chemical moiety or moieties are immobilized on the surface in that region. Thus, an array may have probes that include protein and/or targets that include protein. By "immobilized" is meant that the moiety or moieties are stably associated with the substrate surface in the region, such that they do not separate from the region under conditions of using the array, e.g., hybridization and washing and stripping conditions. As is known in the art, the moiety or moieties may be covalently or non-covalently bound to the surface in the region. For example, each region may extend into a third dimension in the case where the substrate is porous while not having any substantial third dimension measurement (thickness) in the case where the substrate is non-porous. An array may contain more than ten, more than one hundred, more than one thousand more than ten thousand features, or even more than one hundred thousand features, in an area of less than 20 cm$^2$ or even less than 10 cm$^2$. For example, features may have widths (that is, diameter, for a round spot) in the range of from about 0.1 μm to about 1.0 cm. In other embodiments each feature may have a width in the range of about 1.0 μm to about 1.0 mm, such as from about 5.0 μm to about 500 μm, and including from about 10 μm to about 200 μm. Non-round features may have area ranges equivalent to that of circular features with the foregoing width (diameter) ranges. A given feature is made up of chemical moieties, e.g., nucleic acids, proteins, etc., that bind to (e.g., hybridize to) the same target (e.g., target nucleic acid, target protein), such that a given feature corresponds to a particular target. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide. Such interfeature areas typically will be present where the arrays are formed by processes involving drop deposition of reagents but may not be present when, for example, light directed synthesis fabrication processes are used. It will be appreciated though, that the interfeature areas, when present, could be of various sizes and configurations. An array is "addressable" in that it has multiple regions (sometimes referenced as "features" or "spots") of the array) of different moieties (for example, different polynucleotide sequences or proteins) such that a region at a particular predetermined location (an "address") on the array will detect a particular target or class of targets (although a feature may incidentally detect non-targets of that feature). The target for which each feature is specific is, in representative embodiments, known. An array feature is generally homogenous in composition and concentration and the features may be separated by intervening spaces (although arrays without such separation can be fabricated).

In the case of an array, the "target" will be referenced as a moiety in a mobile phase (typically fluid), to be detected by probes ("target probes") which are bound to the substrate at the various regions. However, either of the "target" or "target probes" may be the one which is to be detected by the other (thus, either one could be an unknown mixture of polynucleotides to be detected by binding with the other). "Addressable sets of probes" and analogous terms refer to the multiple regions of different moieties supported by or intended to be supported by the array surface.

The term "sample" as used herein relates to a material or mixture of materials, containing one or more components of interest. Samples include, but are not limited to, samples obtained from an organism or from the environment (e.g., a soil sample, water sample, etc.) and may be directly obtained from a source (e.g., such as a biopsy or from a tumor) or indirectly obtained e.g., after culturing and/or one or more processing steps. In one embodiment, samples are a complex mixture of molecules, e.g., comprising at least about 50 different molecules, at least about 100 different molecules, at least about 200 different molecules, at least about 500 different molecules, at least about 1000 different molecules, at least about 5000 different molecules, at least about 10,000 molecules, etc.

The term "genome" refers to all nucleic acid sequences (coding and non-coding) and elements present in any virus, single cell (prokaryote and eukaryote) or each cell type in a metazoan organism. The term genome also applies to any naturally occurring or induced variation of these sequences that may be present in a mutant or disease variant of any virus or cell type. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism.

For example, the human genome consists of approximately $3.0 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome X's (female) for a total of 46 chromosomes. A genome of a cancer cell may contain variable numbers of each chromosome in addition to deletions, rearrangements and amplification of any subchromosomal region or DNA sequence. In certain aspects, a "genome" refers to nuclear nucleic acids, excluding mitochondrial nucleic acids; however, in other aspects, the term does not exclude mitochondrial nucleic acids. In still other aspects, the "mitochondrial genome" is used to refer specifically to nucleic acids found in mitochondrial fractions.

By "genomic source" is meant the initial nucleic acids that are used as the original nucleic acid source from which the probe nucleic acids are produced, e.g., as a template in the nucleic acid amplification and/or labeling protocols.

If a surface-bound polynucleotide or probe "corresponds to" a chromosomal region, the polynucleotide usually contains a sequence of nucleic acids that is unique to that chromosomal region. Accordingly, a surface-bound polynucleotide that corresponds to a particular chromosomal region usually specifically hybridizes to a labeled nucleic acid made from that chromosomal region, relative to labeled nucleic acids made from other chromosomal regions.

A "design file" is typically provided by an array manufacturer and is a file that embodies all the information that the array designer from the array manufacturer considered to be pertinent to array interpretation. For example, Agilent Technologies supplies its array users with a design file written in the XML language that describes the geometry as well as the biological content of a particular array.

An "array layout" or "array characteristics", refers to one or more physical, chemical or biological characteristics of the array, such as positioning of some or all the features within the array and on a substrate, one or more feature dimensions, or some indication of an identity or function (for example, chemical or biological) of a moiety at a given location, or how the array should be handled (for example, conditions under which the array is exposed to a sample, or array reading specifications or controls following sample exposure).

The phrase "oligonucleotide bound to a surface of a solid support" or "probe bound to a solid support" or a "target bound to a solid support" refers to an oligonucleotide or mimetic thereof, e.g., PNA, LNA or UNA molecule that is immobilized on a surface of a solid substrate, where the substrate can have a variety of configurations, e.g., a sheet, bead, particle, slide, wafer, web, fiber, tube, capillary, microfluidic channel or reservoir, or other structure. In certain embodiments, the collections of oligonucleotide elements employed herein are present on a surface of the same planar support, e.g., in the form of an array. It should be understood that the terms "probe" and "target" are relative terms and that a molecule considered as a probe in certain assays may function as a target in other assays.

As used herein, a "test nucleic acid sample" or "test nucleic acids" refer to nucleic acids comprising sequences whose quantity or degree of representation (e.g., copy number) or sequence identity is being assayed. Similarly, "test genomic acids" or a "test genomic sample" refers to genomic nucleic acids comprising sequences whose quantity or degree of representation (e.g., copy number) or sequence identity is being assayed.

As used herein, a "reference nucleic acid sample" or "reference nucleic acids" refers to nucleic acids comprising sequences whose quantity or degree of representation (e.g., copy number) or sequence identity is known. Similarly, "reference genomic acids" or a "reference genomic sample" refers to genomic nucleic acids comprising sequences whose quantity or degree of representation (e.g., copy number) or sequence identity is known. A "reference nucleic acid sample" may be derived independently from a "test nucleic acid sample," i.e., the samples can be obtained from different organisms or different cell populations of the sample organism. However, in certain embodiments, a reference nucleic acid is present in a "test nucleic acid sample" which comprises one or more sequences whose quantity or identity or degree of representation in the sample is unknown while containing one or more sequences (the reference sequences) whose quantity or identity or degree of representation in the sample is known. The reference nucleic acid may be naturally present in a sample (e.g., present in the cell from which the sample was obtained) or may be added to or spiked in the sample.

A "negative control" probe or feature refers to a probe or feature that is designed not to bind with any of the sequences in the sample that is applied to the array on which the negative control probe or feature resides.

A "CGH array" or "aCGH array" refers to an array that can be used to compare DNA samples for relative differences in copy number. In general, an aCGH array can be used in any assay in which it is desirable to scan a genome with a sample of nucleic acids. For example, an aCGH array can be used in location analysis as described in U.S. Pat. No. 6,410,243, the entirety of which is incorporated herein. In certain aspects, a CGH array provides probes for screening or scanning a genome of an organism and comprises probes from a plurality of regions of the genome. In one aspect, the array comprises probe sequences for scanning an entire chromosome arm, wherein probes targets are separated by at least about 500 bp, at least about 1 kbp, at least about 5 kbp, at least about 10 kbp, at least about 25 kbp, at least about 50 kbp, at least about 100 kbp, at least about 250 kbp, at least about 500 kbp and at least about 1 Mbp. In another aspect, the array comprises probes sequences for scanning an entire chromosome, a set of chromosomes, or the complete complement of chromosomes forming the organism's genome. By "resolution" is meant the spacing on the genome between sequences found in the probes on the array. In some embodiments (e.g., using a large number of probes of high complexity) all sequences in the genome can be present in the array. The spacing between different locations of the genome that are represented in the probes may also vary, and may be uniform, such that the spacing is substantially the same between sampled regions, or non-uniform, as desired. An assay performed at low resolution on one array, e.g., comprising probe targets separated by larger distances, may be repeated at higher resolution on another array, e.g., comprising probe targets separated by smaller distances.

In certain aspects, in constructing the arrays, both coding and non-coding genomic regions are included as probes, whereby "coding region" refers to a region comprising one or more exons that is transcribed into an mRNA product and from there translated into a protein product, while by non-coding region is meant any sequences outside of the exon regions, where such regions may include regulatory sequences, e.g., promoters, enhancers, untranslated but transcribed regions, introns, origins of replication, telomeres, etc. In certain embodiments, one can have at least some of the probes directed to non-coding regions and others directed to coding regions. In certain embodiments, one can have all of the probes directed to non-coding sequences. In certain embodiments, one can have all of the probes directed to coding sequences. In certain other aspects, individual probes comprise sequences that do not normally occur together, e.g., to detect gene rearrangements, for example.

In some embodiments, at least 5% of the polynucleotide probes on the solid support hybridize to regulatory regions of a nucleotide sample of interest while other embodiments may have at least 30% of the polynucleotide probes on the solid support hybridize to exonic regions of a nucleotide sample of interest. In yet other embodiments, at least 50% of the polynucleotide probes on the solid support hybridize to intergenic (e.g., non-coding) regions of a nucleotide sample of interest. In certain aspects, probes on the array represent random selection of genomic sequences (e.g., both coding and non-coding). However, in other aspects, particular regions of the genome are selected for representation on the array, e.g., such as CpG islands, genes belonging to particular pathways of interest or whose expression and/or copy number are associated with particular physiological responses of interest (e.g., disease, such a cancer, drug resistance, toxological responses and the like). In certain aspects, where particular genes are identified as being of interest, intergenic regions proximal to those genes are included on the array along with, optionally, all or portions of the coding sequence corresponding to the genes. In one aspect, at least about 100 bp, 500 bp, 1,000 bp, 5,000 bp, 10,000 kbp or even 100,000 kbp of genomic DNA upstream of a transcriptional start site is represented on the array in discrete or overlapping sequence probes. In certain aspects, at least one probe sequence comprises a motif sequence to which a protein of interest (e.g., such as a transcription factor) is known or suspected to bind.

In certain aspects, repetitive sequences are excluded as probes on the arrays. However, in another aspect, repetitive sequences are included.

The choice of nucleic acids to use as probes may be influenced by prior knowledge of the association of a particular chromosome or chromosomal region with certain disease conditions. International Application WO 93/18186 provides a list of exemplary chromosomal abnormalities and associated diseases, which are described in the scientific literature. Alternatively, whole genome screening to identify new regions subject to frequent changes in copy number can be performed using the methods of the present invention discussed further below.

In some embodiments, previously identified regions from a particular chromosomal region of interest are used as probes. In certain embodiments, the array can include probes which "tile" a particular region (e.g., which have been identified in a previous assay or from a genetic analysis of linkage), by which is meant that the probes correspond to a region of interest as well as genomic sequences found at defined intervals on either side, i.e., 5' and 3' of, the region of interest, where the intervals may or may not be uniform, and may be tailored with respect to the particular region of interest and the assay objective. In other words, the tiling density may be tailored based on the particular region of interest and the assay objective. Such "tiled" arrays and assays employing the same are useful in a number of applications, including applications where one identifies a region of interest at a first resolution, and then uses tiled array tailored to the initially identified region to further assay the region at a higher resolution, e.g., in an iterative protocol.

In certain aspects, the array includes probes to sequences associated with diseases associated with chromosomal imbalances for prenatal testing. For example, in one aspect, the array comprises probes complementary to all or a portion of chromosome 21 (e.g., Down's syndrome), all or a portion of the X chromosome (e.g., to detect an X chromosome deficiency as in Turner's Syndrome) and/or all or a portion of the Y chromosome Klinefelter Syndrome (to detect duplication of an X chromosome and the presence of a Y chromosome), all or a portion of chromosome 7 (e.g., to detect William's Syndrome), all or a portion of chromosome 8 (e.g., to detect Langer-Giedon Syndrome), all or a portion of chromosome 15 (e.g., to detect Prader-Willi or Angelman's Syndrome, all or a portion of chromosome 22 (e.g., to detect Di George's syndrome).

Other "themed" arrays may be fabricated, for example, arrays including whose duplications or deletions are associated with specific types of cancer (e.g., breast cancer, prostate cancer and the like). The selection of such arrays may be based on patient information such as familial inheritance of particular genetic abnormalities. In certain aspects, an array for scanning an entire genome is first contacted with a sample and then a higher-resolution array is selected based on the results of such scanning.

Themed arrays also can be fabricated for use in gene expression assays, for example, to detect expression of genes involved in selected pathways of interest, or genes associated with particular diseases of interest.

In one embodiment, a plurality of probes on the array are selected to have a duplex $T_m$ within a predetermined range. For example, in one aspect, at least about 50% of the probes have a duplex $T_m$ within a temperature range of about 75° C. to about 85° C. In one embodiment, at least 80% of said polynucleotide probes have a duplex $T_m$ within a temperature range of about 75° C. to about 85° C., within a range of about 77° C. to about 83° C., within a range of from about 78° C. to about 82° C. or within a range from about 79° C. to about 82° C. In one aspect, at least about 50% of probes on an array have range of $T_m$'s of less than about 4° C., less then about 3° C., or even less than about 2° C., e.g., less than about 1.5° C., less than about 1.0° C. or about 0.5° C.

The probes on the microarray, in certain embodiments have a nucleotide length in the range of at least 30 nucleotides to 200 nucleotides, or in the range of at least about 30 to about 150 nucleotides. In other embodiments, at least about 50% of the polynucleotide probes on the solid support have the same nucleotide length, and that length may be about 60 nucleotides.

In certain aspects, longer polynucleotides may be used as probes. In addition to the oligonucleotide probes described above, cDNAs, or inserts from phage BACs (bacterial artificial chromosomes) or plasmid clones, can be arrayed. Probes may therefore also range from about 201-5000 bases in length, from about 5001-50,000 bases in length, or from about 50,001-200,000 bases in length, depending on the platform used. If other polynucleotide features are present on a subject array, they may be interspersed with, or in a separately-hybridizable part of the array from the subject oligonucleotides.

In still other aspects, probes on the array comprise at least coding sequences.

In one aspect, probes represent sequences from an organism such as *Drosophila melanogaster, Caenorhabditis elegans*, yeast, zebrafish, a mouse, a rat, a domestic animal, a companion animal, a primate, a human, etc. In certain aspects, probes representing sequences from different organisms are provided on a single substrate, e.g., on a plurality of different arrays.

A "CGH assay" using an aCGH array can be generally performed as follows. In one embodiment, a population of nucleic acids contacted with an aCGH array comprises at least two sets of nucleic acid populations, which can be derived from different sample sources. For example, in one aspect, a target population contacted with the array comprises a set of target molecules from a reference sample and from a test sample. In one aspect, the reference sample is from an organism having a known genotype and/or phenotype, while the test sample has an unknown genotype and/or phenotype or a genotype and/or phenotype that is known and is different from that of the reference sample. For example, in one aspect, the reference sample is from a healthy patient while the test sample is from a patient suspected of having cancer or known to have cancer.

In one embodiment, a target population being contacted to an array in a given assay comprises at least two sets of target populations that are differentially labeled (e.g., by spectrally distinguishable labels). In one aspect, control target molecules in a target population are also provided as two sets, e.g., a first set labeled with a first label and a second set labeled with a second label corresponding to first and second labels being used to label reference and test target molecules, respectively.

In one aspect, the control target molecules in a population are present at a level comparable to a haploid amount of a gene represented in the target population. In another aspect, the control target molecules are present at a level comparable to a diploid amount of a gene. In still another aspect, the control target molecules are present at a level that is different from a haploid or diploid amount of a gene represented in the target population. The relative proportions of complexes formed labeled with the first label vs. the second label can be used to evaluate relative copy numbers of targets found in the two samples.

In certain aspects, test and reference populations of nucleic acids may be applied separately to separate but identical arrays (e.g., having identical probe molecules) and the signals from each array can be compared to determine relative copy numbers of the nucleic acids in the test and reference populations.

Methods to fabricate arrays are described in detail in U.S. Pat. Nos. 6,242,266; 6,232,072; 6,180,351; 6,171,797 and 6,323,043. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods as described in those patents.

Following receipt by a user, an array will typically be exposed to a sample and then read. Reading of an array may be accomplished by illuminating the array and reading the location and intensity of resulting fluorescence at multiple regions on each feature of the array. For example, a scanner may be used for this purpose is the AGILENT MICROARRAY SCANNER manufactured by Agilent Technologies, Palo, Alto, Calif. or other similar scanner. Other suitable apparatus and methods are described in U.S. Pat. Nos. 6,518,556; 6,486,457; 6,406,849; 6,371,370; 6,355,921; 6,320,196; 6,251,685 and 6,222,664. Scanning typically produces a scanned image of the array which may be directly inputted to a feature extraction system for direct processing and/or saved in a computer storage device for subsequent processing. However, arrays may be read by any other methods or apparatus than the foregoing, other reading methods including other optical techniques or electrical techniques (where each feature is provided with an electrode to detect bonding at that feature in a manner disclosed in U.S. Pat. Nos. 6,251,685, 6,221,583 and elsewhere).

An array is "addressable" when it has multiple regions of different moieties, i.e., features (e.g., each made up of different oligonucleotide sequences or proteins) such that a region (i.e., a "feature" or "spot" of the array) at a particular predetermined location (i.e., an "address") on the array will detect a particular solution phase nucleic acid sequence or protein. Array features are typically, but need not be, separated by intervening spaces.

Figure 2:
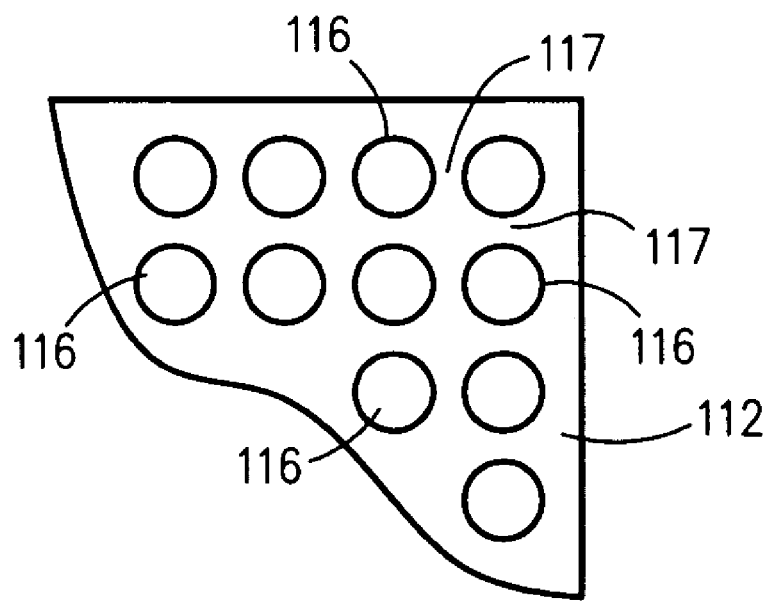
FIG. 2 illustrates an enlarged view of a portion of the array of FIG. 1.

An exemplary array is shown in FIGS. 1-2, where the array shown in this representative embodiment includes a contiguous planar substrate 110 carrying an array 112 disposed on a surface 111*b* of substrate 110. It will be appreciated though, that more than one array (any of which are the same or different) may be present on surface 111*b*, with or without spacing between such arrays. That is, any given substrate may carry one, two, four or more arrays disposed on a surface of the substrate and depending on the use of the array, any or all of the arrays may be the same or different from one another and each may contain multiple spots or features. The one or more arrays 112 usually cover only a portion of the surface 111*b*, with regions of the surface 111*b* adjacent the opposed sides 113*c*, 113*d* and leading end 113*a* and trailing end 113*b* of slide 110, not being covered by any array 112. An opposite surface 111*a* of the slide 110 typically does not carry any arrays 112. Each array 112 can be designed for testing against any type of sample, whether a trial sample, reference sample, a combination of them, or a known mixture of biopolymers such as polynucleotides. Substrate 110 may be of any shape, as mentioned above.

As mentioned above, array 112 contains multiple spots or features 116 of oligomers, e.g., in the form of polynucleotides, and specifically oligonucleotides. As mentioned above, all of the features 116 may be different, or some or all could be the same. The interfeature areas 117 could be of various sizes and configurations. Each feature carries a predetermined oligomer such as a predetermined polynucleotide (which includes the possibility of mixtures of polynucleotides). It will be understood that there may be a linker molecule (not shown) of any known types between the surface 111b and the first nucleotide.

Substrate 110 may carry on surface 111a, an identification code, e.g., in the form of bar code (not shown) or the like printed on a substrate in the form of a paper label attached by adhesive or any convenient means. The identification code may contain information relating to array 112, where such information may include, but is not limited to, an identification of array 112, i.e., layout information relating to the array(s), etc.

In the case of an array in the context of the present application, the "target" may be referenced as a moiety in a mobile phase (typically fluid), to be detected by "probes" which are bound to the substrate at the various regions.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids and/or proteins, are used interchangeably.

A "property" of an array, as used herein refers to a characteristic of an array that may be measured through analysis and calculation based on signals received during reading (e.g., scanning or other method of obtaining signals from) the array, and which may be used as a measure of quality of the array. Properties include, but are not limited to, noise, signal-to noise, background signal, signal intensity, uniformity/non-uniformity, etc.

A "probe signal", "probe value" or "probe signal value" refers to the observed signal obtained from the probe, i.e., the signal from a probe bound to a target, including "true" signal (i.e., from the target that the probe was designed to bind with) and offset, such as from cross-hybridization and other noise factors, including background.

When one item is indicated as being "remote" from another, this is referenced that the two items are not at the same physical location, e.g., the items are at least in different buildings, and may be at least one mile, ten miles, or at least one hundred miles apart.

"Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

A "processor" references any hardware and/or software combination which will perform the functions required of it. For example, any processor herein may be a programmable digital microprocessor such as available in the form of a mainframe, server, or personal computer. Where the processor is programmable, suitable programming can be communicated from a remote location to the processor, or previously saved in a computer program product. For example, a magnetic or optical disk may carry the programming, and can be read by a suitable disk reader communicating with each processor at its corresponding station.

Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference except insofar as they may conflict with those of the present application (in which case the present application prevails).

Methods, Systems and Computer Readable Media

Figure 3:
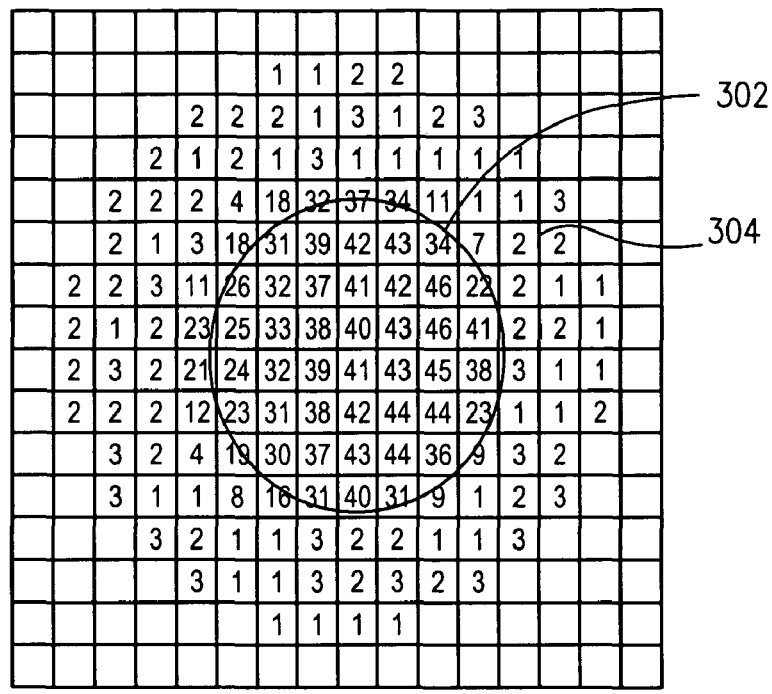
FIG. 3 illustrates a pixel-based result from scanning a disk-shaped feature of a chemical array.

Scanning of a feature by an optical scanning device or radiometric scanning device generally produces a scanned image comprising a rectilinear grid of pixels, with each pixel having a corresponding signal intensity. FIG. 3 shows a portion of a scanned image of a chemical array that includes a pixel-based image of a disk-shaped feature of a chemical array. In FIG. 3, the feature corresponds to a disk-shaped region 302 of pixels having relatively high signal intensities. Surrounding the feature 302 is a ring-like region 304 of pixels with relatively low measured intensities. The portion of the scanned image shown in FIG. 3 is thus conceptually equivalent to a digital, black-and-white photograph of the feature taken with light within a narrow range of wavelengths. Generally, the location of the disk-shaped region 302 corresponding to a feature is determined by various scanned image-to-scanned-chemical-array alignment techniques and procedures.

It is desirable for the signal intensities, or counts, of pixels within the area of a pixel-based scanned image corresponding to a feature to be relatively uniform. Similarly, it is also desirable for the signal intensities within background regions surrounding features to be relatively uniform. Non-uniform signal intensity distributions generally indicate the occurrence of one or more error or noise conditions that may prevent meaningful data from being collected from the feature.

Figure 4:
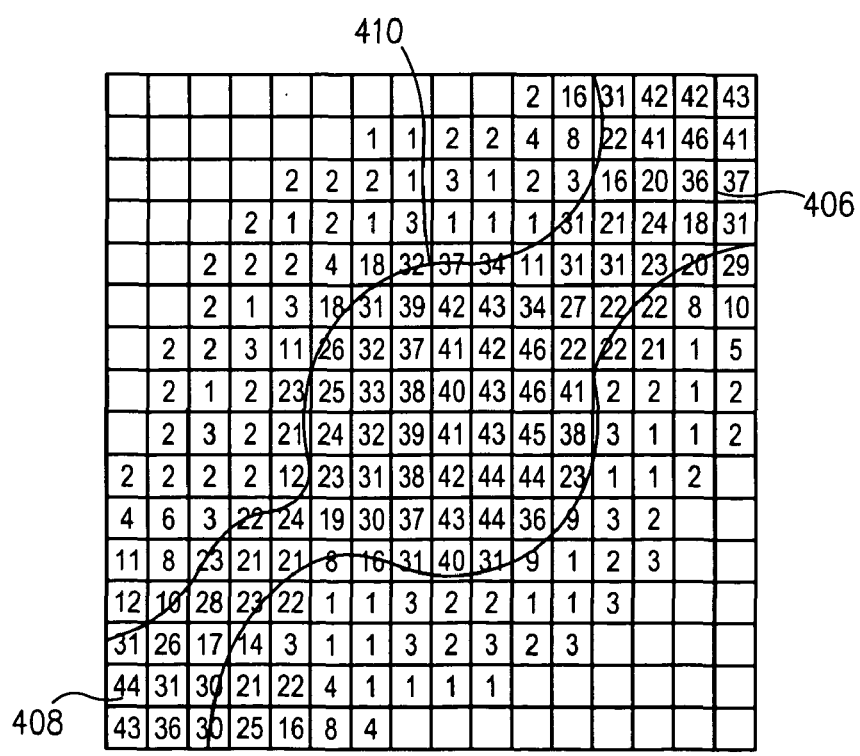
FIGS. 4-6 illustrate various non-uniform signal intensity distributions within a scanned optical image of a chemical array feature.
Figure 5:
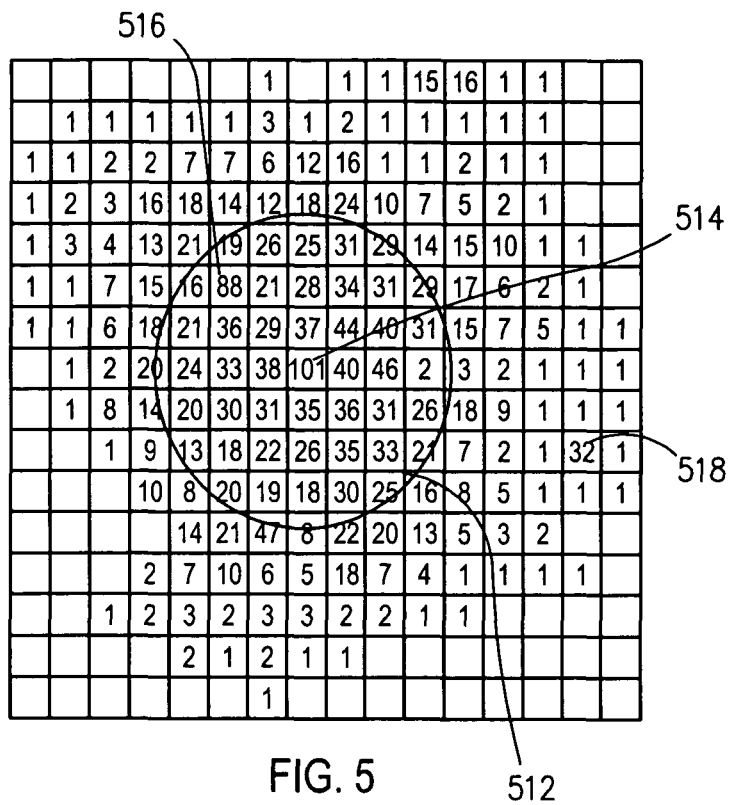
Figure 6:
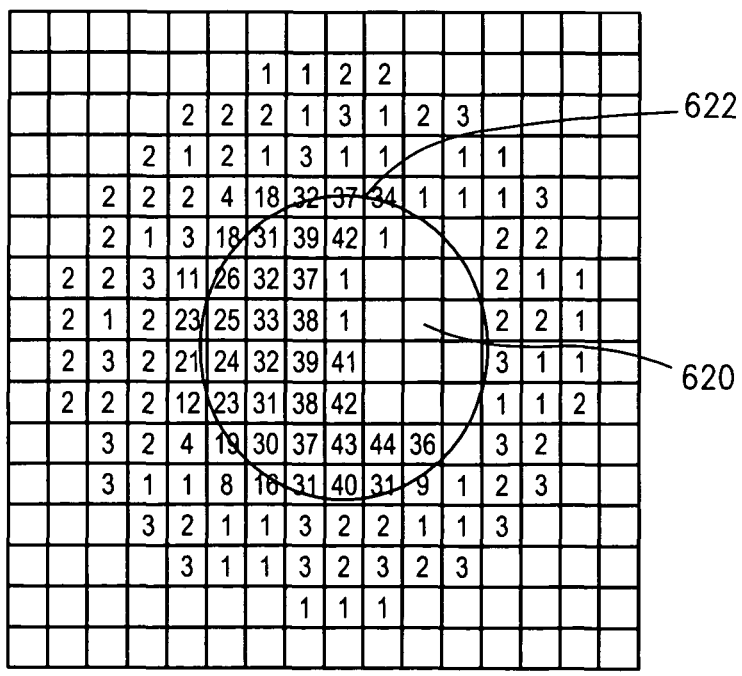

FIGS. 4-6 illustrate various non-uniform signal intensity distributions within a scanned image of a chemical array feature. In FIG. 4, for example, relatively large signal intensities are seen in regions 406 and 408 at the upper right, and lower left, of the scanned image as well as within the disk-shaped area 410 corresponding to a feature. Such non-uniform distribution of signal intensities may indicate defects in the preparation of the chemical array, including defects in the synthesis of probe molecules bound to the chemical array, contamination of the surface of the chemical array with a chromophore that responds to impinging light in a similar fashion to the response by the chromophore with which target molecules are labeled, flaws in the scanning device, artifacts introduced in the labeling, hybridization and/or washing steps, or other such defects. In FIG. 5 the signal intensities within the feature 512 are relatively uniform, with the exception of a number of extremely high, outlying signal intensities in individual pixels, such as pixels 514 and 516. In addition, the surrounding local background region is fairly uniform with the exception of a high outlying pixel 518. Such outlying pixel intensities may represent scanner measurement errors or defects in digital processing and digital representation of the scanned data.

In FIG. 6 a relatively large area 620 within a feature 622 has produced no signal, and therefore represents a significant spatial non-uniformity of pixel intensities. A condition such as that shown in FIG. 6 may arise when probe molecules are not uniformly bound to the surface of the chemical array within a feature, because of overlying contamination that masks the signal, or due to a scratch to the surface, or for other reasons. In the situations illustrated in FIGS. 4-6, the sum of the pixel intensities within the disk-shaped region of the optical image corresponding to a feature may produce a total signal intensity, or count, for the feature that does not reflect the theoretical count that would be produced by scanning the feature were the one or more error conditions or noise conditions not present. Such scanned features suffering from non-uniform pixel intensities need to be recognized during processing of data scanned from a molecular array and flagged as outlier features, to prevent reporting of flawed and erroneous experimental results.

The present invention is directed to identifying outlier features and outlier feature backgrounds within scanned images of chemical arrays. The variance of signal intensities within a feature or feature background is compared to a maximum allowable variance calculated based on a dynamic variance model in order to determine whether or not the region of a scanned image of a molecular array corresponding to a feature or feature background contains adequately uniform pixel-based signal intensities within. The dynamic non-uniform outlier algorithms provided greatly reduce the time to tune feature extraction protocols as array platforms that are processed change. By automatically determining coefficients of the variance models used to determine outliers, the present invention avoid the requirements to re-tune the model each time a different array platform is to be analyzed, as the present variance models need be tuned only once for any given scanner. As array platforms change, the variance models dynamically and automatically tune to changes introduced by the change in array platform, as the coefficients of the variance models may be determined independent of the scanner used to scan the chemical array.

Figure 7:
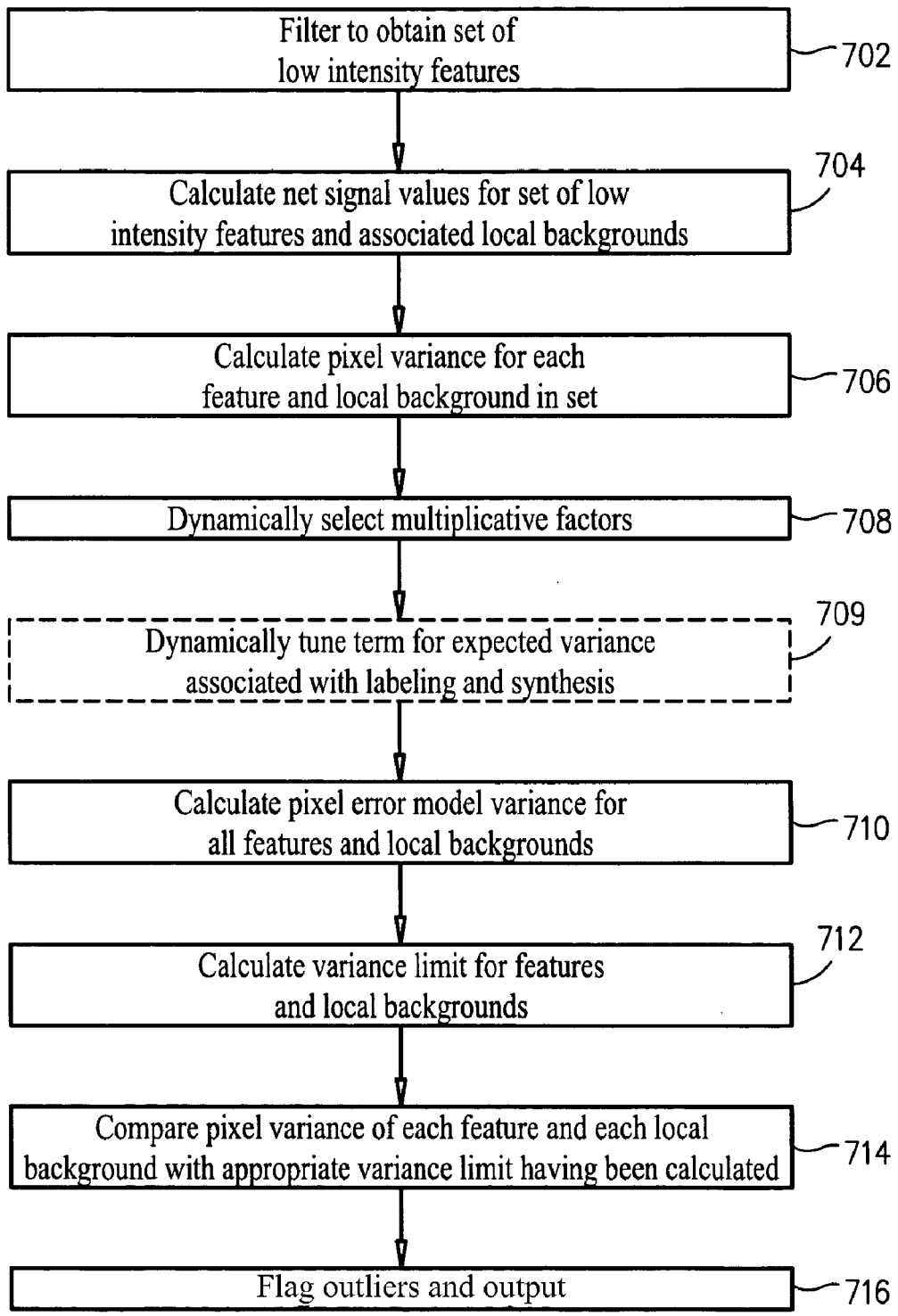
FIG. 7 illustrates processing events that may be carried out for identifying outlier features and/or outlier feature backgrounds, according to an embodiment of the present invention.

Data processing techniques employed in outlier detection involve application of various statistical measurements on the per-pixel counts, or pixel-based signal intensities measured for a particular feature or feature background and included in a digital representation of the scanned image of the chemical array. A chemical array scanner produces a raw digital representation including a count, or signal intensity, for each pixel within the digital representation. FIG. 7 illustrates processing events that may be carried out for identifying outlier features and/or outlier feature backgrounds, according to an embodiment of the present invention. At event 702, the chemical array data is filtered to obtain a set of low intensity features. An example of the set of low intensity features that may be filtered for are the set of negative control (NC) features that exist on the chemical array. Negative controls may typically be identified via a design file associated with the array being considered, or with some other code identifiers provided by the manufacturer of the chemical array. Further, the set of negative control features are typically filtered to remove any saturated features, using currently available feature extraction filtering techniques. Alternatively, event 702 may be carried out to obtain some other predefined set of low intensity features. For example, the filtering may be performed to obtain the lowest X % (e.g., 1% or some other predefined number) of the intensities of the feature signals, or some other statistically identified set of low intensity features. Alternatively, the filtering may use features that are determined to have signal in the range of negative control signals. Co-pending, commonly owned application Ser. No. 11/580,744 filed Oct. 12, 2006 and titled "Methods and Systems for Removing Offset Bias in Chemical Array Data" discloses details about methods for determining features that are considered to be in the range of negative control signals, and is hereby incorporated herein in its entirety, by reference thereto.

This set of low intensity features (NC_Set) and the local background regions associated with the set of low intensity features (Bk_Set) identified by the filtering process of event 702 are used in subsequent calculations in the events described hereafter. At event 704, net signals ($S_{net}$) are calculated from the measured signals ($S_{measured}$) for each background region and feature in the selected sets as follows:

$$S_{net} = S_{measured} - S_{offset} \quad (1)$$

For each measured per-pixel count, or pixel-based signal intensity, the net signal is obtained by subtracting a signal offset "$s_{offset}$" from the measured signal "$s_{measured}$." The signal offset may be automatically provided by the scanner device or may be empirically determined by identifying a minimal signal in the digital representation of the chemical array produced by scanning the chemical array and processing the scanned data. Signal offset may vary from scanner to scanner and from scanner manufacturer to scanner manufacturer. There may not be a scanner offset, and in such instances, $S_{net} = S_{measured}$.

At event 706, the pixel variance within each feature and local background in the set is calculated. An estimate of the variance of the per-pixel counts within an area (e.g., within a feature or within a designated local background area) of a digital representation of a chemical array corresponding to a feature or feature background may be obtained as follows:

$$\sigma^2_{s_{net}} = \frac{1}{n-1} \sum_{i=1}^{n} (s_{net} - \bar{s}_{net})^2 \quad (2)$$

where
 $\sigma$=standard deviation;
 $\sigma^2$=variance;
 n=the number of pixels within the feature or feature background;
 $s_{net}$=net signal per pixel; and $$\bar{s}_{net} = \frac{1}{n} \sum_{i=1}^{n} s_{net}.$$

Thus, the variance of pixel counts or pixel-based signal intensities within a feature or feature background can be straightforwardly calculated from the net signals obtained from the digital representation of the scanned image of a chemical array. The pixel variance (PixVar) and pixel standard deviation (PixSDev) can be measured by the feature extraction software (e.g., Agilent Feature Extraction software) from the pixels of the scanned image inputted thereto.

In order to determine whether the pixel counts or pixel-based signal intensities within a feature or feature background are sufficiently uniform, the calculated variance "$\sigma^2_{s_{net}}$" needs to be compared to a threshold value to determine whether or not the calculated variance $\sigma^2_{s_{net}}$ falls below the threshold value and therefore is acceptable. In one embodiment of the present invention, the calculated variance model "$\sigma_{model}^2$" is a linear combination of three different, independent model variances:

$$\sigma_{model}^2 = \sigma_{labelingandfeaturesynthesis}^2 + \sigma_{counting}^2 + \sigma_{noise}^2 \quad (3)$$

The model variance "$\sigma_{labelingandfeaturesynthesis}^2$" is the variance expected for non-uniformities associated with target-molecule labeling, feature synthesis, and other solution and surface and chemistry effects. The model variance "$\sigma_{counting}^2$" is the variance expected in scanning measurement, or counting, error. The model variance "$\sigma_{noise}^2$" is the expected variance due to electronic noise in the scanner, background-level signal noise produced by the glass substrate of the molecular array, and other such noise.

Figure 8A:
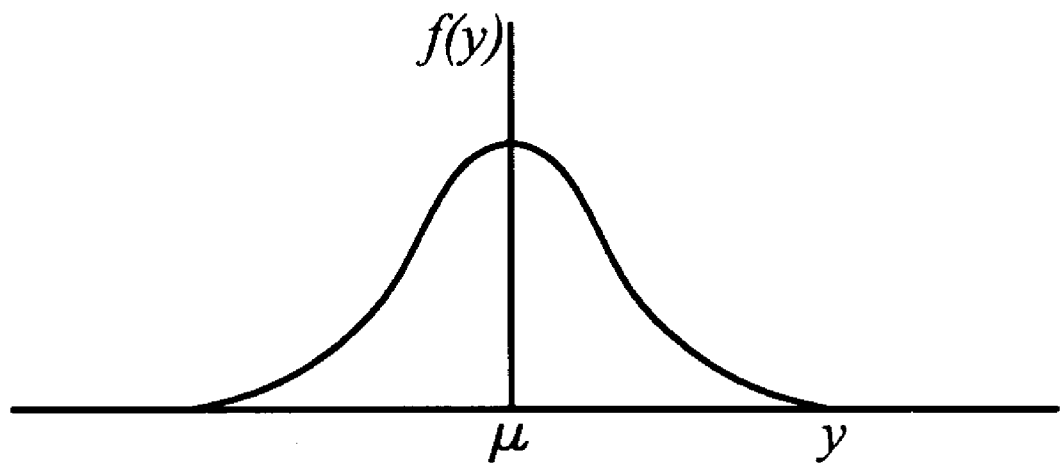
FIG. 8A illustrates a generalized normal distribution.

In one embodiment of the present invention, the non-uniformity associated with labeling and feature synthesis is considered to be normally distributed. FIG. 8A illustrates a generalized normal distribution, described by the following expression:

$$f(y) = \frac{e^{-(y-\mu)^2/2\sigma^2}}{\sigma\sqrt{2\Pi}} \quad (4)$$

where
y=measured quantity;
μ=mean; and
σ=standard deviation.

Figure 8B:
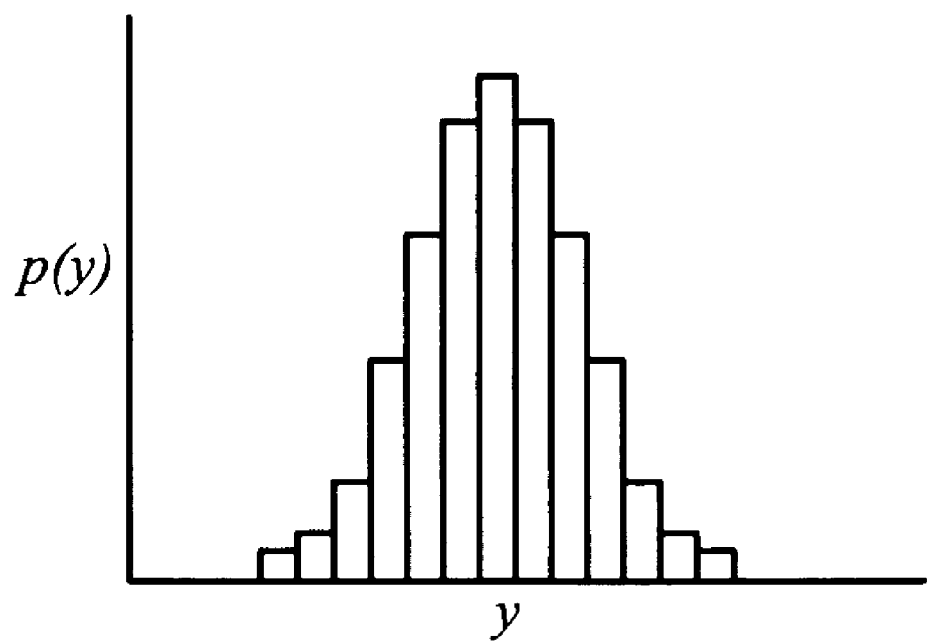
FIG. 8B illustrates a binomial distribution.

In the variance model of equation (3), the non-uniformity associated with scanner measurement error, i.e., counting error, may be considered to be distributed according to a Poisson distribution. FIG. 8B illustrates a binomial distribution, described by the following expression:

$$p(y) = \binom{n}{y} p^y q^{n-y} \quad (5)$$

where
p(y)=probability of y positive outcomes,
p=probability of a positive outcome,
q=probability of a negative outcome, and
n=counts, time intervals, etc.

A Poisson distribution is the limit of the binomial distribution as n approaches infinity. The Poisson distribution is expressed as follows:

$$p(y) = \frac{\lambda^y}{y!} e^{-\lambda} \quad (6)$$

where
$\lambda = \bar{y}$, and
$\bar{y}$=mean value of y.

The non-uniformity associated with electronic scanner noise and glass-substrate-background-level noise may be considered to be a constant, in the described embodiment, or may alternatively be dynamically calculated in a manner as described below.

The model variance $\sigma_{model}^2$ may be alternatively expressed as:

$$\sigma_{model}^2 = A\bar{s}_{net}^2 + B\bar{s}_{net} + C \quad (7)$$

where
$A\bar{s}_{net}^2 = \sigma_{labelingandfeaturesynthesis}^2$,
$B\bar{s}_{net} = \sigma_{counting}^2$, and
$C = \sigma_{noise}^2$.

The coefficients A, B and C may each include two factors:

$$A = A_s * A_d, \quad (8)$$

$$B = B_s * B_d, \text{ and} \quad (9)$$

$$C = C_s * C_d \quad (10)$$

where the factors containing subscript "s" refer to scanner-dependent multipliers, and the factors containing subscript "d" refer to factors that are dynamically determined for each array.

For a given scanner type (e.g., a scanner from a particular manufacturer, or a particular scanner model) initial coefficients $A_s$, $B_s$ and $C_s$ may be determined as initial values to be further modified by dynamic tuning (e.g., with dynamic multipliers $A_d$, $B_d$ and $C_d$) as described herein. Since as noted, scanner can vary from manufacturer to manufacturer or even from model to model, these initial coefficients may be different for different makes or models of scanners. Further, there may be different initial coefficients for different channels of the same scanner. The scanner-dependent multipliers can be estimated from analysis of large numbers of chemical arrays from different batches of arrays, different users, as well as different processes for preparing and hybridizing the arrays. These arrays are also scanned by the same manufacturer or model of scanner.

One manner of tuning the scanner-dependent multipliers is to empirically vary the scanner-dependent multipliers, in parallel with the dynamic calculation of the array-dependent multipliers (those factors with a "d" subscript). A plot of pixel variance versus net signal can be made and a line can be drawn that represents the variance limit using the equation that results from the draft set of "s" coefficients and the calculated array-dependent (subscript "d") multipliers. If the variance limit set by the equation is too tight, it will cut into the bulk of the data, causing too many features to be called non-uniform (e.g., see FIG. 12A). When this occurs, another set of scanner-dependent multipliers may be substituted that are larger than the previously used scanner-dependent multipliers to yield a variance limit line that is higher. An optimal set of coefficients can be arrived at by iterating this process, each time increasing or decreasing the limit line, to arrive at a plot such as shown in FIG. 12B, for example.

In addition, if there is replicate feature data on an array, or replicate arrays, validation can be performed to show that features (or background regions) that are called non-uniform when using the selected multipliers, do indeed have signals that are much different from their replicates.

In order to automatically and dynamically tune the coefficients of the variance model to a particular array, a histogram of the net signal values and a histogram of the pixel variance values for the features as well as the local backgrounds of the set of low intensity features is prepared for each channel of signals to be analyzed for that array. The signal intensity behavior of this set of features is functionally related to the variance expected in scanning measurement, or counting: thus, this distribution is used to dynamically calculate the $B_d$ term. The pixel variance of this set of features is functionally related to the expected variance due to electronic noise in the scanner, or constant background-level signal noise produced by the glass substrate of the molecular array, and other such noise: thus, this distribution is used to dynamically calculate the $C_d$ term. That is, multiplicative factors may be selected (event 708) from the histograms described to automatically and dynamically tune the factors $B_d$ and $C_d$ in equations (9) and (10) to the array being analyzed, based on the signal intensity values and pixel variance values of the features and local backgrounds in the selected set.

Figure 9A:
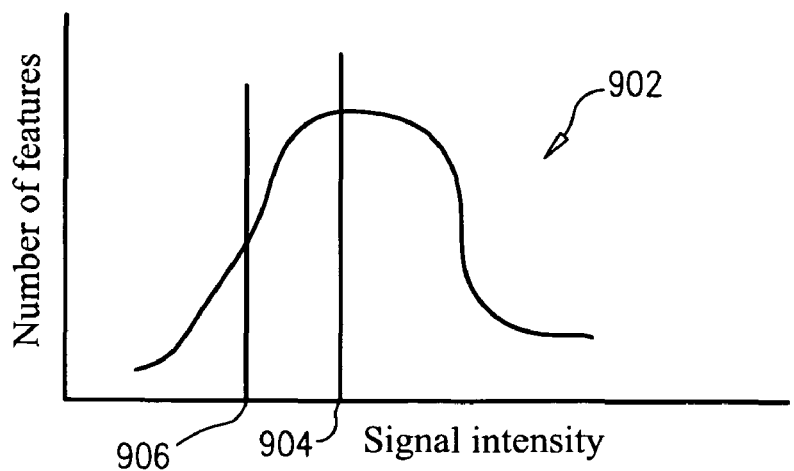
FIG. 9A illustrates a histogram of signal intensity values for negative control features filtered from scanning a chemical array.

For example, FIG. 9A illustrates a histogram 902 of the signal intensity values for negative control features filtered from scanning an array in a manner as described above. A multiplicative factor $B_d$ may be selected from the histogram values in FIG. 9A by taking the signal intensity value at a predetermined percentile value of the values in the histogram 902. For example, $B_d$ may be selected as the 50$^{th}$ percentile value 904 of the histogram 902, or any other value identified by setting a predetermined percentile value in the range from 1$^{st}$ to 100$^{th}$ percentile values. This predetermined percentile value may be automatically preset to a percentage value in the algorithm. Although any predetermined percentage value may be preset, it has been found that the 25$^{th}$ percentile value 906 provides good results.

Figure 9B:
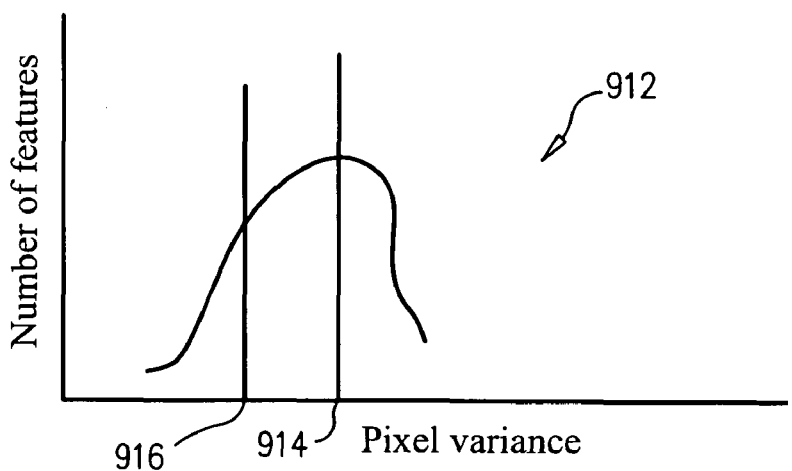
FIG. 9B illustrates a histogram of the pixel variance values for the negative control features referred to in FIG. 9A.

FIG. 9B illustrates a histogram 912 of the pixel variance values for negative control features filtered from scanning an array in a manner as described above. A multiplicative factor $C_d$ may be selected from the histogram values in FIG. 9B by taking the pixel variance value at a predetermined percentile value of the values in the histogram 912. For example, $C_d$ may be selected as the 50$^{th}$ percentile value 914 of the histogram 912, or any other value identified by setting a predetermined percentile value in the range from 1$^{st}$ to 100$^{th}$ percentile values. This predetermined percentile value may be automatically preset to a percentage value in the algorithm. Although any predetermined percentage value may be preset, it has been found that the 25$^{th}$ percentile value 916 provides good results.

Multipliers $C_d$ and $B_d$ are also selected for the local backgrounds of the selected set of features, by assembling histograms of the local background signal intensities and pixel variances, in the same manner as described above with regard to the features in the selected set. The multipliers are then selected from these histograms in the same manner as described above with regard to selection of multipliers in FIGS. 9A-9B.

Multiplier selection for features and local backgrounds as described above, is carried out for each channel of signals to be analyzed, as these multipliers can vary from channel to channel.

Once multiplier selection has been performed, the coefficients B and C for the pixel error model (equation (7)) may be calculated as follows:

$$B = B_s * B_d \quad (11)$$

$$C = C_s * C_d \quad (12)$$

Note that coefficients B and C are calculated separately for features, local backgrounds, and that thus, for each channel, a pair of B coefficients (one for features, one for local backgrounds) and a pair of C coefficients (one for features, one for local backgrounds) are calculated.

At event 710, the pixel error model variance is calculated for feature signal intensity variance and local background signal intensity variance for each feature and for each channel, using the pixel error model having been dynamically tuned to the current array being analyzed. At event 712, a variance limit (i.e., "confidence limit") may be calculated for feature variance and a variance limit may be calculated for local background variance. These confidence limits are calculated for each channel. Event 714 includes comparing pixel variance of each feature and each local background with appropriate variance limit having been calculated. Event 716 includes flagging outliers and output.

Figure 10:
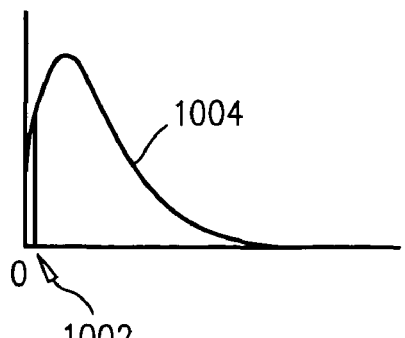
FIG. 10 illustrates a representative $\chi^2$ distribution.

In one non-limiting embodiment (since other bases for setting confidence limits may be substituted), variance limits $\sigma^2_{max}$ may be calculated based on an assumption that the following expression is distributed according to a $\chi^2$ distribution with n−1 degrees of freedom, where n is the number of feature or feature background pixels:

$$\frac{(n-1)\hat{\sigma}^2}{\sigma^2} \quad (13)$$

where
$\sigma^2$ is the true feature or feature background variance under the assumption that the model is valid, and the feature or feature background is not an outlier. A representative $\chi^2$ distribution 1004 is shown in FIG. 10. The mathematical function for the $\chi^2$ distribution shown in FIG. 10 can be found in U.S. Pat. No. 6,993,172.

The threshold value may be determined by selecting a lower bound "$\chi_x$" (1002 in FIG. 10) such that the probability that the $\chi^2$-distributed expression $$\frac{(n-1)\hat{\sigma}^2}{\sigma^2}$$

is greater than 1-α/2, where the probability 1-α/2 is the area under the distribution curve 1004 to the right of the lower bound "$\chi_x$" 1002, according to the following expression:

$$p\left[\chi_x^2 \leq \frac{(n-1)\hat{\sigma}^2}{\sigma^2}\right] = 1 - \alpha/2 \quad (14)$$

By rearranging the above expression, an equivalent expression is obtained:

$$p\left[\sigma^2 \leq \frac{(n-1)\hat{\sigma}^2}{\chi_x^2}\right] = 1 - \alpha/2 \quad (15)$$

Thus:

$$\sigma^2_{max} = \frac{(n-1)\hat{\sigma}^2}{\chi_x^2} \quad (16)$$

As noted earlier, rather than manually tuning the variance model for the variance expected for non-uniformities associated with target-molecule labeling, feature synthesis, and other solution and surface and chemistry effects (i.e., by manually tuning the constant $A = A_0$) automatic and dynamic tuning of this variance term may alternatively be carried out. As with the dynamic tuning of the variance terms for the variance expected in scanning measurement, or counting, and expected variance due to electronic noise in the scanner, background-level signal noise produced by the glass substrate of the molecular array, and other such noise, the dynamic adjustment of the variance term for expected variance for non-uniformities associated with target-molecule labeling, feature synthesis and other solution and surface chemistry effects is calculated separately for features and local background regions of the selected set, and for each channel.

Figure 11:
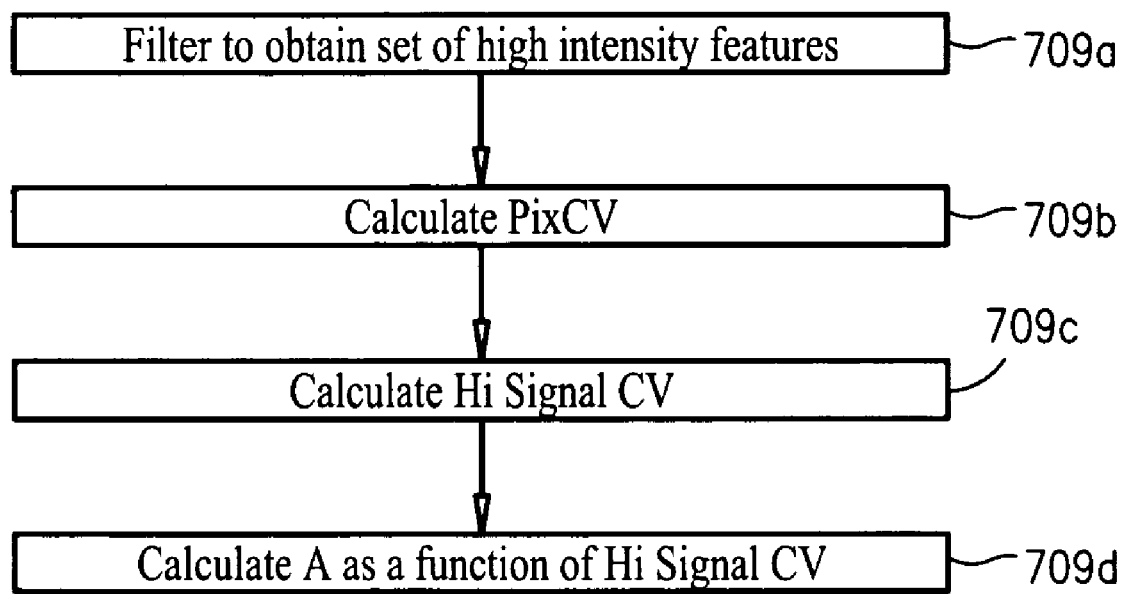
FIG. 11 illustrates events that may be optionally performed during the optional event 709 shown in FIG. 7.

FIG. 11 illustrates events that may be performed during the optional event 709 in order to dynamically tune terms for expected variance associated with labeling and synthesis. For these operations, a different set of features and associated local background regions are selected from the population of features and local background regions on the array. The set of features that are selected at event 709a for these operations are features in the relatively high end of the signal range of the features.

There are multiple different ways that such filtering may be performed. With each way, the feature signals are first filtered to remove those features determined to be saturated, according to techniques currently available in feature extraction software, prior to selection of high signal features for further processing. In one approach, features having net signals higher than a signal specified in the feature extraction software may be selected based on a negative control spread (NegControl Spread) such as described in co-pending application Ser. No. 11/580,744, with the constraint that the features selected must have signals greater than some multiplier times the Spread, e.g., greater than 100*Spread, or some other multiplier times the Spread. This multiplier can be predefined by the system, or, optionally, may be user settable. Another approach involves filtering to select those features having net signals greater than a predefined threshold based on a specified percentile of the feature intensity values when arranged in a histogram. For example, it may be specified to select those features that are not saturated and have a net signal intensity value greater than the $90^{th}$ percentile net signal intensity value.

Still another approach is to select net signals of features over a dynamic limit that is calculated from a feature extraction signal error model, like that used in Rosetta Resolver software, optionally including calculation of an additive error term in accordance with techniques described in application Ser. No. 11/139,896 filed May 26, 2005 and titled "Method and System for Quantifying Random Errors and Any Spatial-Intensity Trends Present in Microarray Data Sets". Application Ser. No. 11/139,896 is hereby incorporated herein, in its entirety, by reference thereto. An example of such a dynamic limit follows:

If {(NetSignal*ProportionalErrorTerm)>AdditiveErrorTerm}, then the feature having that NetSignal is selected into the "high signal" set, along with the net signal for its local background area, each to be used for further processing; where NetSignal=the net signal of the feature being considered by comparison to dynamic limiting (where NetSignal is defined by raw mean signal—scanner offset, e.g., see equation (1) above);

ProportionalErrorTerm=the multiplicative error associated with the feature, where multiplicative error is proportional to the signal level. Multiplicative error is described in application Ser. No. 11/139,896. The error in high signal features is dominated by this type of error. This term may be similar to an inter-array % CV term.

AdditiveErrorTerm=a term for a constant level of noise, that is seen across all features. Features having low signal have noise that is dominated by additive error type noise, since the proportional error term is low, given the low level of signal. Often, the AdditiveErrorTerm is correlated with statistics involving negative control spread, residual of fit after background subtraction, etc.

Another approach involves selecting those features whose net signals are included in a range calculated as a function of the net signals of the negative control probes. For example, features having net signals as follows may be selected:

NetSignal>NC_Mult*NC_Metric where

NetSignal=the net signal of the feature being considered by comparison to dynamic limiting;

NC_Mult=an empirically determined multiplier, e.g., "10" or some other multiplier; and NC_Metric=a statistical metric characterizing the negative control signals, such as standard deviation, interquartile range, a predetermined percentile value (e.g., $75^{th}$ percentile), etc.

After selection of the set of high intensity features, the pixel coefficient of variation (PixCV) is calculated for each feature in the high signal set at event 709b according to:

PixCV=PixSD/NetSignal

Where

PixCV=the pixel coefficient of variation as a ratio;

PixSD is the standard deviation of the pixel intensities within the feature; and NetSignal=the net signal of the feature.

Next, a metric (HiSignalCV) is calculated at event 709c as a function of the set of PixCV's calculated in event 709b. For example, such functions may be predetermined percentile values of the PixCV values when arranged in a histogram (e.g., 25th percentile, $50^{th}$ percentile, or $90^{th}$ percentile, etc.). At event 709d, A is calculated as A=HiSignalCV*HiSignalMult, where HiSignalMult is a composite of $A_s*A_d$, wherein $A_s$ need only be manually tuned once for a given scanner type, and wherein $A_d$ is dynamically tuned for each different hybridized array. Alternatively, a set of PixCV values that correspond to high signal features can be found by plotting the PixCV values versus the net signals of the features and, using standard algorithms, finding the PixCV of the asymptote at high signal range.

Figure 12A:
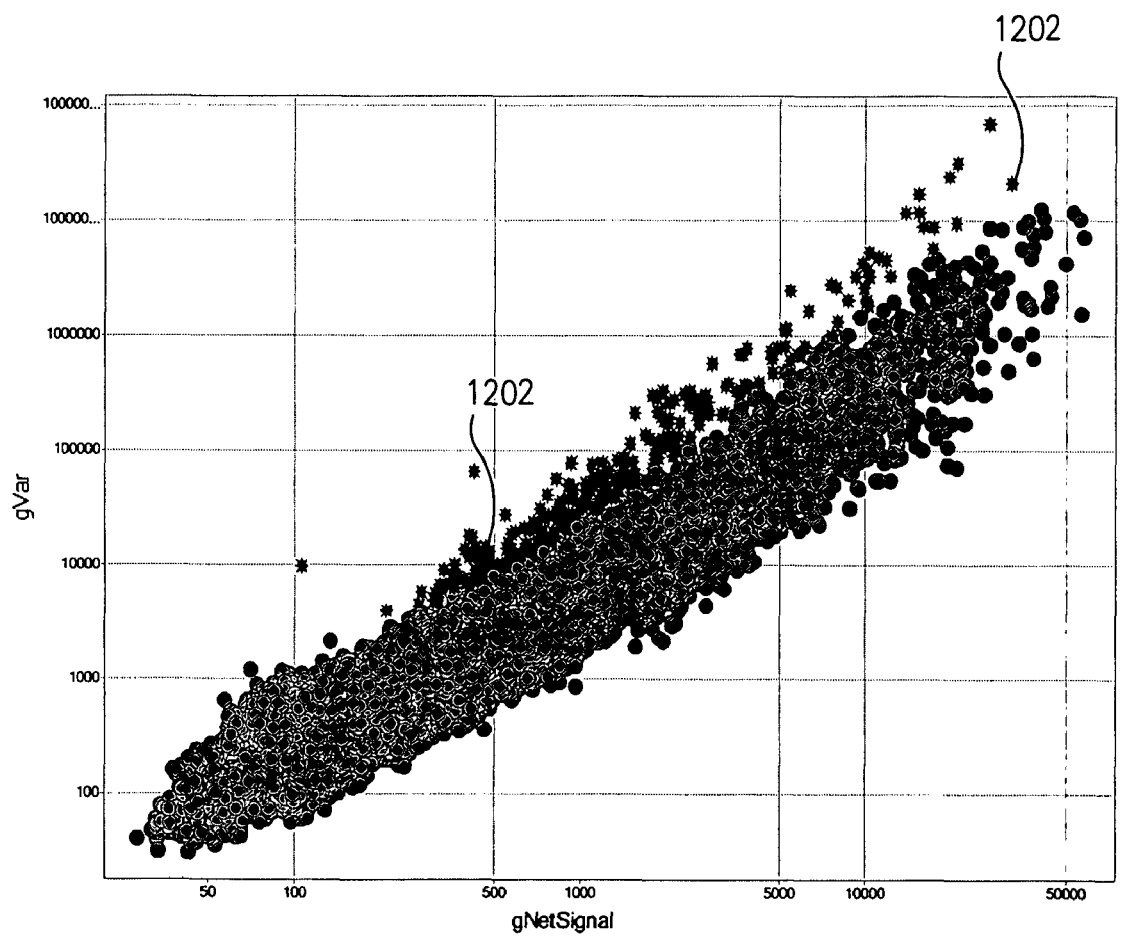
FIG. 12A shows flagging results (features flagged as non-uniform outliers) for signals from features of a scanned chemical array, when using a manually tuned variance model.
Figure 12B:
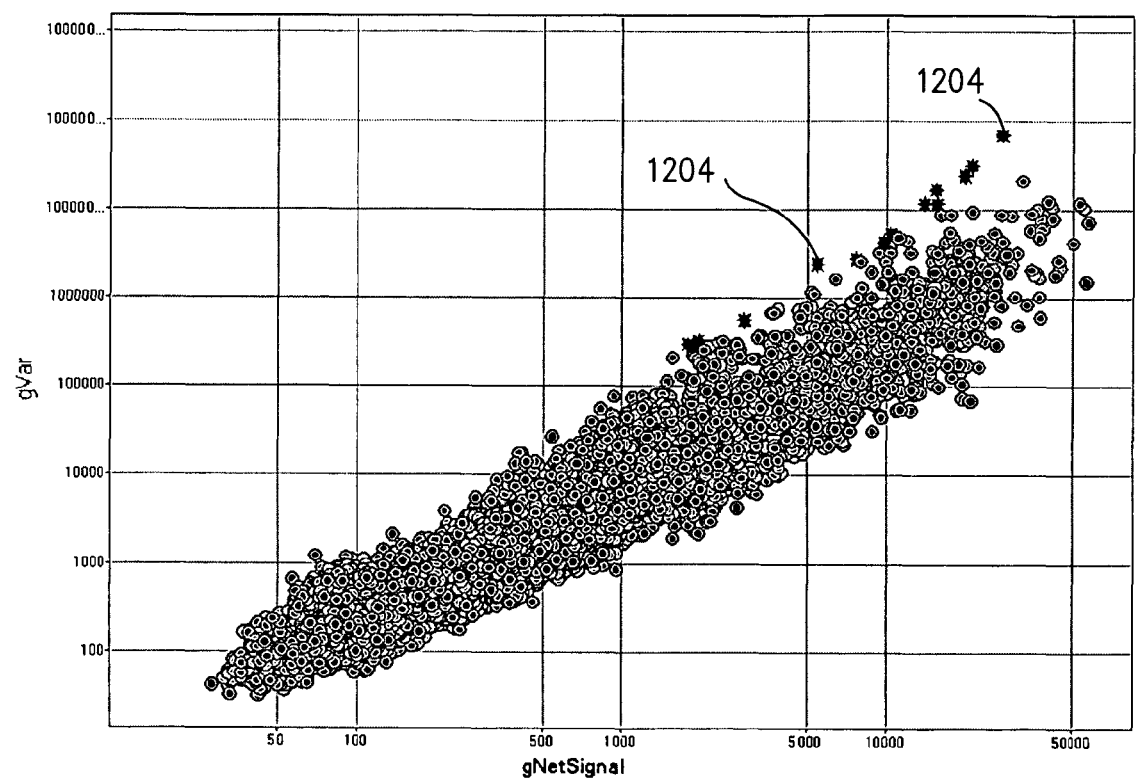
FIG. 12B shows flagging results (features flagged as non-uniform outliers) for signals from the same features of the same scanned chemical array analyzed in FIG. 12A, but using an automatic, dynamically adjusting variance model according to an embodiment of the present invention.

FIGS. 12A-12B show plots of feature net signals taken from the green channel of a scanner for an array processed versus pixel variance, with indication of the features flag as being nonuniform outliers. The same feature data are used for each plot. The only difference is in the equation used to generate the variance limit line. FIG. 12A shows the flagging results (features flagged as nonuniform outliers are indicated as the star-shaped features 1202) when using the manually tuned variance model described in U.S. Pat. No. 6,993,172. In this instance, the system used to produce this array was different from the system used in the original manual tuning of the variance model (manual tuning as described in U.S. Pat. No. 6,832,163, which is hereby incorporated herein, in its entirety, by reference thereto). Differences in the system may include different labeling, hybridization, or washing parameters, or different scanner used. One can see that the manually tuned parameters are not fitting this array well. Visual observation of FIG. 12A readily shows that features that appear to be within the general grouping of the features plotted, and hence should most likely not be considered non-uniform outliers, have been flagged.

FIG. 12B shows the same plot of net signals versus variance values as shown in FIG. 12A, but where the features flagged as non-uniform outliers (star-shaped features 1204) were flagged using an automatic, dynamic tuning algorithm according to the present invention. In this case, the scanner dependent multipliers $A_s$, $B_s$ and $C_s$ were tuned for an Agilent scanner and the array-dependent multipliers $A_d$, $B_d$ and $C_d$ were determined dynamically, for this array, as described above. In FIG. 12B it can be readily observed that the algorithm has adapted better to the changed conditions posed by the new type of system, as only a few true outlier features have been flagged as non-uniform outliers 1204, and features within the main grouping of features plotted have not been flagged, as a general rule.

Figure 13:
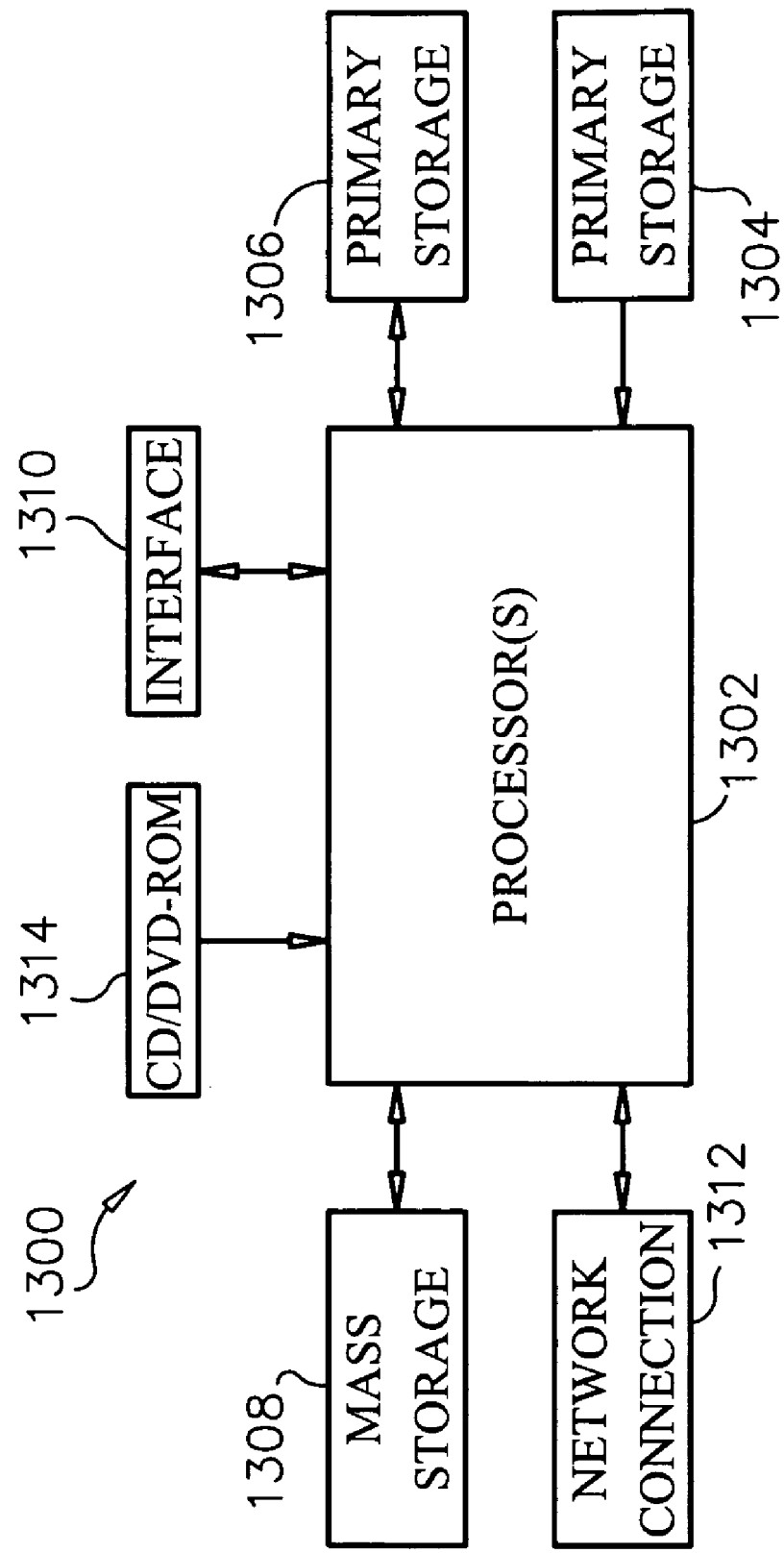
FIG. 13 is a schematic illustration of a typical computer system that may be used in performing procedures described herein.

FIG. 13 is a schematic illustration of a typical computer system that may be used to perform procedures described above. The computer system 1300 includes any number of processors 1302 (also referred to as central processing units, or CPUs) that are coupled to storage devices including primary storage 1306 (typically a random access memory, or RAM), primary storage 1304 (typically a read only memory, or ROM). As is well known in the art, primary storage 1304 acts to transfer data and instructions uni-directionally to the CPU and primary storage 1306 is used typically to transfer data and instructions in a bi-directional manner Both of these primary storage devices may include any suitable computer-readable media such as those described above. A mass storage device 1308 is also coupled bi-directionally to CPU 1302 and provides additional data storage capacity and may include any of the computer-readable media described above. Mass storage device 1308 may be used to store programs, data and the like and is typically a secondary storage medium such as a hard disk that is slower than primary storage. It will be appreciated that the information retained within the mass storage device 1308, may, in appropriate cases, be incorporated in standard fashion as part of primary storage 1306 as virtual memory. A specific mass storage device such as a CD-ROM or DVD-ROM 1314 may also pass data uni-directionally to the CPU.

CPU 1302 is also coupled to an interface 1310 that includes one or more input/output devices such as a user interface, video monitors, scanners or other readers, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 1302 optionally may be coupled to a computer or telecommunications network using a network connection as shown generally at 1312. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for calculating net signal values, pixel variance and other calculations described herein, may be stored on mass storage device 1308 or 1314 and executed on CPU 1308 in conjunction with primary memory 1306.

In addition, embodiments of the present invention further relate to computer readable media or computer program products that include program instructions and/or data (including data structures) for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, CDRW, DVD-ROM, or DVD-RW disks; magneto-optical media such as floptical disks; and hardware devices that are specially configured to store and perform program instructions, such as read-only memory devices (ROM) and random access memory (RAM). However, computer readable media are not intended to include carrier waves, such as radio waves. Examples of program instructions include both machine code, such as produced by a compiler, and files containing higher level code that may be executed by the computer using an interpreter.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of identifying a non-uniform measured signal distribution in a region of a scanned image of a chemical array, said method comprising:
    providing an automatic, dynamically adjustable variance model for measured signal distributions within regions of the chemical array;
    determining a variance of measured signals within the region;
    determining whether or not the region contains a non-uniform measured signal distribution by comparing the determined variance of measured signals within the region to the variance model; and
    displaying results indicating whether or not the region contains a non-uniform measure signal distribution.

2. The method of claim 1, wherein the dynamic automatically adjustable variance model includes coefficients of the variance model that are dependent upon a scanner used to scan the image and coefficients that are dependent upon the characteristics of the chemical array, wherein the coefficients that are dependent upon the characteristics of the chemical array are dynamically determined by the model.

3. The method of claim 1 further including determining a variance threshold from the automatic, dynamically adjustable variance model, and wherein comparing the determined variance of measured signals within the region to the variance model comprises comparing the determined variance of measured signals within the region to the determined variance threshold.

4. The method of claim 3, wherein the scanned image comprises pixels, each pixel associated with a count representing a signal measured from a corresponding portion of the chemical array.

5. The method of claim 4, wherein the variance model is a linear combination of model variance terms.

6. The method of claim 5, wherein said model variance terms include:
    a variance term arising from non-uniformities associated with target-molecule labeling, feature synthesis, probe molecule application, and other solution and surface chemistry effects;
    an automatic, dynamically adjusting variance term arising from non-uniformities associated with scanner counting errors, that automatically and dynamically adjusts to the pixels of the scanned image; and
    an automatic, dynamically adjusting variance term arising from non-uniformities associated with electronic noise in a scanner, background-level signal noise arising from a chemical array substrate, and other noise, that automatically and dynamically adjusts to the pixels of the scanned image.

7. The method of claim 6, wherein said variance term arising from non-uniformities associated with target-molecule labeling, feature synthesis, probe molecule application, and other solution and surface chemistry effects is an automatic, dynamically adjusting variable that adjusts to the pixels of the scanned image.

8. The method of claim 6, wherein non-uniformities associated with scanner counting errors are modeled by a Poisson distribution.

9. The method of claim 4, wherein the variance model is an expression including a mean pixel count for the region as a variable.

10. The method of claim 3, wherein said calculating a variance threshold from the variance model further includes assuming a chi-squared distribution for one less than the number of pixels multiplied by the model variance and divided by the theoretical variance of measured signals within the region, and, based on the chi-squared distribution assumption, selecting a threshold variance value below which the determined variance of measured signals within the region has a high probability of indicating an acceptably uniform distribution of measured signals within the region.

11. The method of claim 1, wherein the region is selected from among a feature and a feature background.

12. The method of claim 1, wherein the variance model is provided according to chemical and physical properties of the chemical array, electronic and physical properties of a scanning device, and experimental conditions to which the chemical array is exposed.

13. A non-transitory computer-readable medium having computer executable instructions stored thereon, for performing the method of claim 1.

14. A method of dynamically tuning a variance model to an instance of a hybridized chemical array, said method comprising the steps of:
inputting signal intensity values produced from scanning a region of the hybridized array;
defining a variance model as a sum of factors multiplied by multiplicative coefficients, wherein the multiplicative coefficients for the respective factors are each a composite of a scanner-dependent multiplier and an array-dependent multiplier;
dynamically calculating the array-dependent multipliers;
determining a variance of measured signals within the region;
determining whether or not the region contains a non-uniform measured signal distribution by comparing the determined variance of measured signals within the region to the variance model; and
displaying results indicating whether or not the region contains a non-uniform measure signal distribution.

15. The method of claim 14, wherein the scanner-dependent multipliers are tuned from empirical analysis of large numbers of arrays having different characteristics, such that the scanner-dependent multipliers stay the same in the variance model as long as the same scanner or model of scanner is being used with various arrays, and wherein the array-dependent multipliers are dynamically calculated for each individual array that the variance model is applied to.

16. A system for identifying a non-uniform measured signal distribution in a region of a scanned image of a chemical array, the system comprising:
a digital representation of the measured signals in the region of the scanned image of the chemical array stored within a memory component;
an automatic, dynamically adjustable variance model for measured signal distributions within regions of the chemical array stored within a memory component; and
a computational processing engine that calculates a variance of measured signals within the region and compares the calculated variance with the variance model to determine whether or not the region contains a non-uniform measured signal distribution by comparing the determined variance of measured signals within the region to the variance model.

17. The system of claim 16, wherein the automatic, dynamically adjusting variance model further includes a variance threshold to which the computational processing engine compares the calculated variance.

18. The system of claim 16, wherein the digital representation of the measured signals in the region of the scanned image of the chemical array comprises a number of pixels, each pixel associated with a count representing a signal measured from a corresponding portion of the chemical array.

19. The system of claim 16, wherein the automatic, dynamically adjusting variance model is a linear combination of model variance terms.

20. The system of claim 19, wherein said model variance terms include:
a variance term arising from non-uniformities associated with target-molecule labeling, feature synthesis, probe molecule application, and other solution and surface chemistry effects;
an automatic, dynamically adjusting variance term arising from non-uniformities associated with scanner counting errors, that automatically and dynamically adjusts to the pixels of the scanned image; and
an automatic, dynamically adjusting variance term arising from non-uniformities associated with electronic noise in a scanner, background-level signal noise arising from a chemical array substrate, and other noise, that automatically and dynamically adjusts to the pixels of the scanned image.

21. The system of claim 20, wherein said variance term arising from non-uniformities associated with target-molecule labeling, feature synthesis, probe molecule application, and other solution and surface chemistry effects is an automatic, dynamically adjusting variable that adjusts to the pixels of the scanned image.

22. The system of claim 20, wherein non-uniformities associated with scanner counting errors are modeled by a Poisson distribution.

23. The system of claim 16, wherein the variance model is an expression including a mean pixel count for the region as a variable.

24. The system of claim 16, wherein the variance model is based on chemical and physical properties of the chemical array, electronic and physical properties of a scanning device, and experimental conditions to which the chemical array is exposed.

* * * * *